United States Patent [19]

McCulloch et al.

[11] Patent Number: 4,996,380
[45] Date of Patent: Feb. 26, 1991

[54] PROCESS FOR EXTRACTING META-DICHLOROBENZENE FROM ISOMER MIXTURES WITH MIXED ALKALI METAL EXCHANGED X ZEOLITE ADSORBENTS

[75] Inventors: Beth McCulloch, Barrington; Michael G. Gatter, Elk Grove Village, both of Ill.

[73] Assignee: UOP, Des Plaines, Ill.

[21] Appl. No.: 433,500

[22] Filed: Nov. 8, 1989

[51] Int. Cl.$^5$ ............................................. C07C 17/38
[52] U.S. Cl. ..................................................... 570/211
[58] Field of Search ......................................... 570/211

[56] References Cited

U.S. PATENT DOCUMENTS

| | | | |
|---|---|---|---|
| 2,882,244 | 4/1959 | Milton | 252/455 |
| 2,958,708 | 11/1960 | Fleck et al. | 260/650 |
| 2,985,589 | 5/1961 | Broughton et al. | 210/34 |
| 3,040,777 | 6/1962 | Carson et al. | 137/625.15 |
| 3,422,848 | 1/1969 | Liebman et al. | 137/625.15 |
| 3,706,812 | 12/1972 | De Rosset et al. | 269/674 SA |
| 4,571,441 | 2/1986 | Miwa et al. | 570/211 |
| 4,642,397 | 2/1987 | Zinnen et al. | 568/394 |

FOREIGN PATENT DOCUMENTS 278680 4/1988 European Pat. Off. .

OTHER PUBLICATIONS

Kuhl, *Zeolites*, vol. 7, Sep. 1987, pp. 451–457.

*Primary Examiner*—Werren B. Lone
*Attorney, Agent, or Firm*—Thomas K. McBride; John F. Spears, Jr.; Jack H. Hall

[57] ABSTRACT

A process for separating the isomers of dichlorobenzene from a feed mixture of the same. Separation of the isomers is effected by selective absorption and desorption and is susceptible to various flow schemes for performing continuous adsorptive separations. The process uses an X-type zeolite adsorbent having a mixture of sodium and potassium ions in the exchangeable cationic sites. The desorbent may be an alkyl benzene, such as toluene, xylene, p-diethylbenzene, etc.

6 Claims, 6 Drawing Sheets

PROCESS FOR EXTRACTING META-DICHLOROBENZENE FROM ISOMER MIXTURES WITH MIXED ALKALI METAL EXCHANGED X ZEOLITE ADSORBENTS

BACKGROUND OF THE INVENTION

1. Field Of The Invention

The field of art to which this invention pertains is the solid bed adsorptive separation of dichlorobenzene (DCB) isomers. More specifically, the invention relates to a process for extracting the meta isomer of dichlorobenzene (m-DCB) from mixtures of DCB isomers employing as the adsorbent X zeolites containing mixed alkali metal cations.

2. Background Information

The individual isomers of dichlorobenzene are useful in a variety of reactions, e.g., as intermediates for making pesticides, pharmaceuticals, peroxides, dyes, etc. The dichlorobenzene isomers are normally prepared by the non-catalytic nuclear chlorination of benzene or chlorobenzene in various solvents. The chlorinating agent comprises certain Lewis acid halides, e.g., hydrogen chloride in both liquid and vapor phase systems. The direct chlorination of chlorobenzene or benzene produces a mixture of dichlorobenzene isomers.

Separation of m-DCB from the other isomers of dichlorobenzene by conventional distillation techniques is difficult due to the close boiling point range of these isomers. The following table shows the boiling points of the isomers.

TABLE 1

| DCB Isomer | Boiling Point (°C.) |
|---|---|
| o-DCB | 180.4 |
| m-DCB | 173.0 |
| p-DCB | 174.1 |

While it is possible to separate o-DCB by distillation from the isomer mixture produced by the process of direct chlorination of chlorobenzene or benzene referred to above, the desired product m-DCB cannot be easily separated from p-DCB by distillation.

Fleck et al U.S. Pat. No. 2,958,708 discloses the adsorptive separation of ortho-dichlorobenzene from meta-dichlorobenzene with sodium-exchanged X zeolite adsorbent, which can be partially exchanged by calcium, magnesium, strontium or barium ions, and an aromatic hydrocarbon, preferably chlorobenzene, desorbent. The process is m-DCB rejective, i.e., m-DCB is non-adsorbed. Another meta-DCB rejective process using at least partially lithium-exchanged sodium-X zeolite and either toluene or 3,4-dichlorotoluene desorbent is disclosed in Japanese Public Disclosure 268636/86. It is also disclosed therein (Table 1 Adsorbent No. 1), that meta-DCB is preferentially adsorbed over para-DCB, when sodium-exchanged X zeolite is the adsorbent with toluene as desorbent, but the selectivity of meta-DCB over ortho-DCB is so low that separation of meta-DCB from isomer mixtures containing ortho-DCB would not be effective. It is apparent that meta-DCB could not be removed in pure form without first removing the ortho-DCB by distillation.

Japanese Public Disclosure 150524/83 discloses the rejective separation of meta-dichlorobenzene from its isomers with a sodium, potassium- or silver-potassium-exchanged Y type zeolite containing at least 90% potassium ions and either 3,4-dichlorotoluene or 4-chloroorthoxylene as desorbent.

Another meta-rejective absorptive (sic) separation is disclosed in EP 278,680 utilizing a high-silica zeolite, TPZ-3 in either sodium- or acid-form, and conventional desorption procedures.

U.S. Pat. No. 4,571,441 discloses a meta-rejective preparation using a Y zeolite exchanged with silver and/or copper ions.

Japanese Public Disclosure 5155/62, to the extent that it appears pertinent, discloses the use of chlorobenzene as desorbent in an adsorptive separation of halogenated aromatic isomers with an X-type zeolite.

Methods for forming the crystalline powders into agglomerates are also known and include the addition of an inorganic binder, generally a clay comprising a silicon dioxide and aluminum oxide, to a high purity zeolite powder in wet mixture. The blended clay-zeolite mixture is extruded into cylindrical type pellets or formed into beads which are subsequently calcined in order to convert the clay to an amorphous binder of considerable mechanical strength. Clays of the kaolin type, water permeable organic polymers and silica may also be used as binders.

The invention herein can be practiced in fixed or moving adsorbent bed systems, but the preferred system for this separation is a countercurrent simulated moving bed system, such as described in Broughton U.S. Pat. No. 2,985,589, incorporated herein by reference. Cyclic advancement of the input and output streams can be accomplished by a manifolding system, which are also known, e.g., by rotary disc valves shown in U.S. Pat. Nos. 3,040,777 and 3,422,848. Equipment utilizing these principles are familiar, in sizes ranging from pilot plant scale (deRosset U.S. Pat. No. 3,706,812) to commercial scale in flow rates from a few cc per hour to many thousands of gallons per hour.

The functions and properties of adsorbents and desorbents in the chromatographic separation of liquid components are well-known, but for reference thereto, Zinnen et al U.S. Pat. No. 4,642,397 is incorporated herein.

Of the above references, only Japanese Public Disclosure 268636/86 discloses a meta-dichlorobenzene extractive process. However, selectivity over the ortho isomer with NaX zeolite is so low ($\alpha_{o/m}=0.94$—Table 1) that meta-DCB could not be effectively separated from ortho-DCB. We have discovered that improved selectivity for m-DCB and particularly over ortho-DCB, can be achieved with an adsorbent which contains certain mixtures of sodium and potassium ions at the ion exchangeable sites. It was entirely unexpected that m-DCB selectivity could be reversed from that of K-exchanged zeolites and also that relativity between m-DCB and o-DCB could be achieved.

A meta-selective process is preferred for purification of DCB isomer mixtures because high purity m-DCB can be obtained when it is extracted over the other isomers.

SUMMARY OF THE INVENTION

In brief summary, the invention is a process for separating m-DCB from the other isomers of dichlorobenzene from a feed mixture comprising a mixture of the isomers. The process comprises contacting the isomers at adsorption conditions with an adsorbent comprising an X zeolite containing combinations of potassium and sodium ions at the cation exchange sites. After contact with the adsorbent, the relatively unadsorbed portion of the feed is removed and the more strongly adsorbed component is recovered using a desorbent comprising an alkyl benzene, e.g., toluene, xylene, or p-diethylbenzene. The preferred desorbent is toluene. Diluents, e.g., saturated aliphatic hydrocarbons, may also be used in admixture with the adsorbent. Preferred as diluents are saturated aliphatic hydrocarbons having less than 13 carbon atoms.

In some instances, as where any o-DCT present in the feed is removed by fractionation, one embodiment of the invention, the separation of m-DCB from p-DCB may be very desirable.

Other embodiments of the present invention encompass specific feed mixtures, desorbent compositions, flow schemes and operating conditions, all of which are hereinafter disclosed in the following discussion of the present invention.

DETAILED DESCRIPTION OF THE INVENTION

Adsorbents to be used in the process of this invention comprise specific crystalline aluminosilicates of molecular sieves, namely X zeolites. The zeolites have known cage structures in which the alumina and silica tetrahedra are intimately connected in an open three-dimensional network to form cage-like structures with window-like pores. The tetrahedra are cross-linked by the sharing of oxygen atoms with spaces between the tetrahedra occupied by water molecules prior to partial or total dehydration of this zeolites. The dehydration of the zeolite results in crystals interlaced with cells having molecular dimensions and thus, the crystalline aluminosilicates are often referred to as "molecular sieves" when the separation which they effect is dependent essentially upon differences between the sizes of shapes of the feed molecules as, for instance, when smaller normal paraffin molecules are separated from larger isoparaffins molecules by using a particular molecular sieve. In the process of this invention, however, the term "molecular sieves", although widely used, is not strictly suitable since the separation of specific aromatic isomers is apparently dependent on differences in electrochemical attraction of the different isomers and the adsorbent rather than on pure physical size or shape differences in the isomer molecules.

In hydrated or partially hydrated form, the preferred crystalline aluminosilicates generally encompass the X-structured zeolites represented by the formula 1 below in terms of moles of metal oxides:

$$(0.9\pm0.2)M_{2/n}O:Al_2O_3:(2.5\pm0.5)SiO_2:yH_2O \qquad \text{Formula 1}$$

where "M" represents at least one cation having a valence of not more than 3, "n" represents the valence of "M" and "y" is a value up to about 9 depending upon the identity of "M" and the degree of hydration of the crystal. These zeolites are described and defined in U.S. Pat. No. 2,882,244. Commercially available zeolites made according to this patent have molar ratios of silica to alumina of about 2.5. More recently, X zeolites have been reported by Kuhl (Zeolites, Vol. 7 Sept. 1987 pp 451-57)), in which the molar ratio of lowered to 2.0, the lowest possible, to obtain the highest exchange capacity. Both have been found to be satisfactory for this invention.

Adsorbents comprising the type X zeolites in which part of the exchangeable cationic sites are occupied by sodium ions and the remainder are occupied by potassium ions are essential to the practice of the invention. The weight ratio of sodium to potassium in the adsorbent preferably ranges from 0.65:1 to 2:1. Typically type X zeolites as initially prepared are predominantly in the sodium form. The sodium ions are partially replaced or exchanged with potassium ions by ion exchange methods well known to those having ordinary skill in the field of crystalline aluminosilicates. Such exchange is generally performed by contacting the zeolite or an adsorbent material containing the zeolite with an aqueous solution of a soluble salt of potassium. After the desired degree of exchange takes place, the zeolite is removed from the aqueous solution, washed, then dried to a desired water content.

Typically, adsorbents used in separative processes such as described herein contain the crystalline material dispersed in an amorphous inorganic matrix or binder, having channels and cavities therein which enable liquid access to the crystalline material. Amorphous material such as silica or silica-alumina mixtures or compounds, such as clays, are typical of such inorganic matrix materials. The binder typically in amounts ranging from 2-25% by weight, aids in forming or agglomerating the crystalline particles of the zeolite which otherwise would comprise a fine powder. The adsorbent may thus be in the form of particles such as extrudates, aggregates, tablets, macrospheres or granules having a desired particle size range, from about 16 to about 40 mesh (Standard U.S. Mesh) (1.9 mm to 250 $\mu$m).

In this process, and particularly the preferred continuous simulated moving bed process, the desorbent must be selected to satisfy the following criteria: First, the desorbent material should displace an extract component from the adsorbent with reasonable mass flow rates without itself being so strongly adsorbed in a following adsorption cycle. Secondly, the desorbent material must be compatible with the particular adsorbent and the particular feed mixture. More specifically, it must not reduce or destroy the critical selectivity of the adsorbent for an extract component with respect to a raffinate component. The desorbent should additionally be easily separable from the feed mixture that is passed into the process. Both the raffinate stream and the extract stream are removed from the adsorbent in admixture with desorbent material and without a method of separating at least a portion of the desorbent material, the purity of the extract product and the raffinate product would not be very high nor would the desorbent material be available for reuse in the process. It is, therefore, contemplated that any desorbent material used in this process will preferably have a substantially different average boiling point than that of the feed mixture, i.e., more than about 5° C. difference, to allow separation of at least a portion of desorbent material from feed components in the extract and raffinate streams by simple fractional distillation, thereby permitting reuse of desorbent material in the process. Finally, desorbent materials should also be materials which are readily available and reasonable in cost. However, a suitable desorbent or desorbents for a particular separation with a specific adsorbent are not always predictable. In the preferred isothermal, isobaric, liquid-phase operation of the process of our invention, we prefer toluene as the material, but other diethylbenzenes may be used, such as xylene and p-diethylbenzene. A saturated, aliphatic hydrocarbon having less than 13 carbon atoms may be used as a diluent in amounts up to about 50% (wt.), increasing the net retention volume for the adsorbed meta-DCB isomer when used with the above discussed adsorbents.

Feed mixtures which can be separated in the process of this invention result from the chlorination of benzene or chlorobenzene which produces a mixture of the isomers: o-DCB, m-DCB, and p-DCB.

Although both liquid and vapor phase operations can be used in many adsorptive separation processes, liquid-phase operation is preferred for this process because of the lower temperature requirements and because of the higher yields of extract product that can be obtained with liquid-phase operation over those obtained with vapor-phase operation. Adsorption conditions will include a temperature range of from about 60° C. to about 200° C., with about 100° C. to about 180° C. being preferred and a pressure sufficient to maintain liquid-phase, ranging from about atmospheric to about 500 psig with from about atmospheric to about 200 psig usually being adequate. Desorption conditions will include the same range of temperatures and pressures as used for adsorption conditions.

At least a portion of the extract stream, which contains the concentrated m-DCB product, and preferably at least a portion of the raffinate stream, from the separation process are passed to separation means, typically fractionators or evaporators, where at least a portion of the desorbent material is separated to produce an extract product and a raffinate product, respectively.

A dynamic testing apparatus is employed to test various adsorbents with a particular feed mixture and desorbent material to measure the adsorption characteristics of retention, capacity and exchange rate. The apparatus used herein consisted of a helical adsorbent chamber of approximately either 70 cc or 14 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such a refractometers, polarimeters and chromatographs can be attached to the outlet line of the chamber and used to detect qualitatively, or determine quantitatively, one or more components in the effluent stream leaving the adsorbent chamber. A pulse test, performed using this apparatus and the following general procedure is used to determine data, e.g., selectivity, for various adsorbent system. The adsorbent is placed in a chamber and filled to equilibrium with a particular desorbent material by passing the desorbent material through the adsorbent chamber. At a convenient time, a pulse of feed containing known concentrations of a tracer and of a particular extract component or of a raffinate component or both, all diluted in desorbent material is injected for a duration of several minutes. Desorbent material flow is resumed, and the tracer and the extract component or the raffinate component (or both) are eluted as in a liquid-solid chromatographic operation. The effluent can be analyzed on-stream or alternatively, effluent samples can be collected periodically and later analyzed separately by analytical equipment and traces of the envelopes or corresponding component peaks developed.

From information derived from the test, adsorbent performance can be rated in terms of void volume, net retention volume (NRV) for an extract or a raffinate component, the rate of desorption of an extract component from the adsorbent and selectivity. The net retention volume of an extract or a raffinate component may be characterized by the distance between the center of the peak envelope of the extract or raffinate component and the center of the peak envelope of the tracer component (void volume) or some other known reference point. Gross retention volume (GRV) is the distance between the center of a peak envelope and the zero abscissa and measured as total ml. of desorbent material pumped during this interval. NRV is also the difference between the respective GRVs and the GRV of the tracer. It is expressed in terms of the volume in cubic centimeters of desorbent material pumped during this time interval represented by the distance between the peak envelopes. The rate of exchange or desorption rate of an extract component with the desorbent material can generally be characterized by the width of the peak envelopes at half intensity. The narrower the peak width, the faster the desorption rate. Selectivity, $\beta$, is determined by the ratio of the net retention volumes of the more strongly adsorbed component to each of the other components.

The examples shown below are intended to further illustrate the process of this invention without unduly limiting the scope and spirit of said process. The examples present test results for various adsorbent and desorbent materials when using the above dynamic testing apparatus.

EXAMPLE I

In this experiment, three pulse tests, as described above, were performed to evaluate the advantage of the present invention in separating metadichlorobenzene from a feed containing o-, m- and p-dichlorobenzene with an X-type zeolite having a 2.5 molar ratio of silica to alumina.

Figure 1:
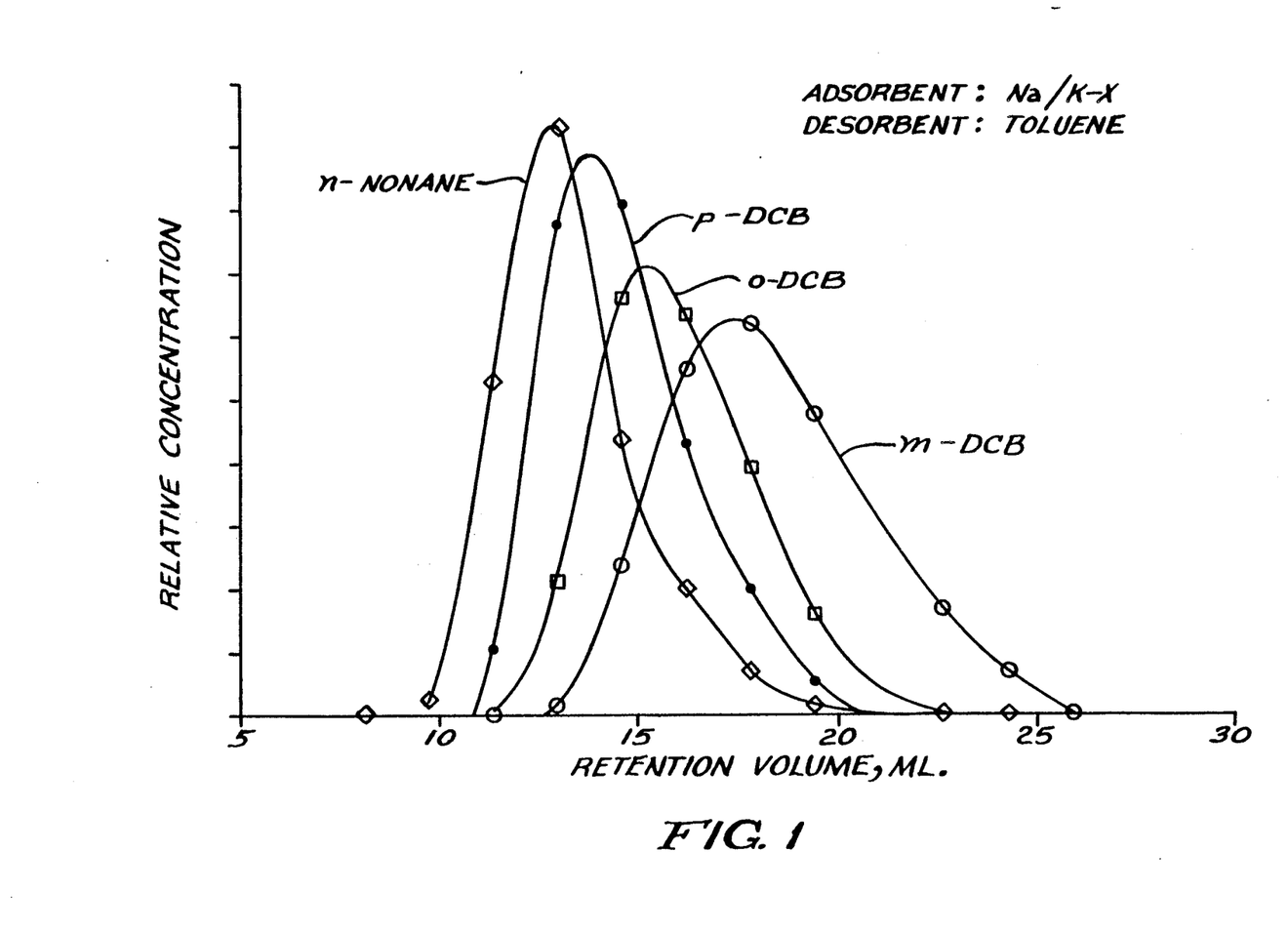
FIGS. 1-3 are chromatographic traces representing the separations of Example I with Na-KX zeolite at a 2.5 molar ratio of silica to alumina ($SiO_2/Al_2O_3$) and various weight ratios of sodium to potassium exchange ions of from (2:1 to 0.65:1) (1.9:1 to 2:3). The desorbent was toluene.
Figure 2:
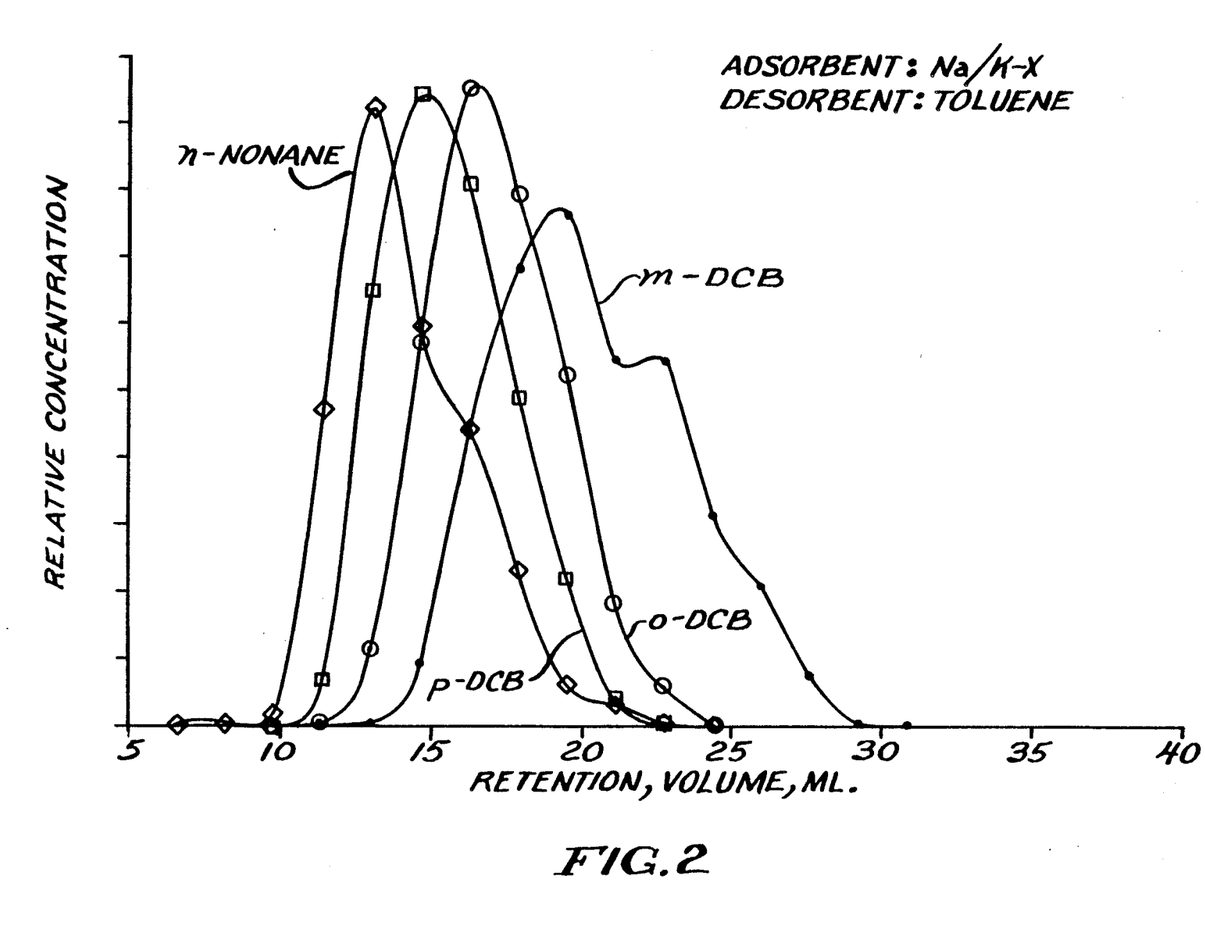
Figure 3:
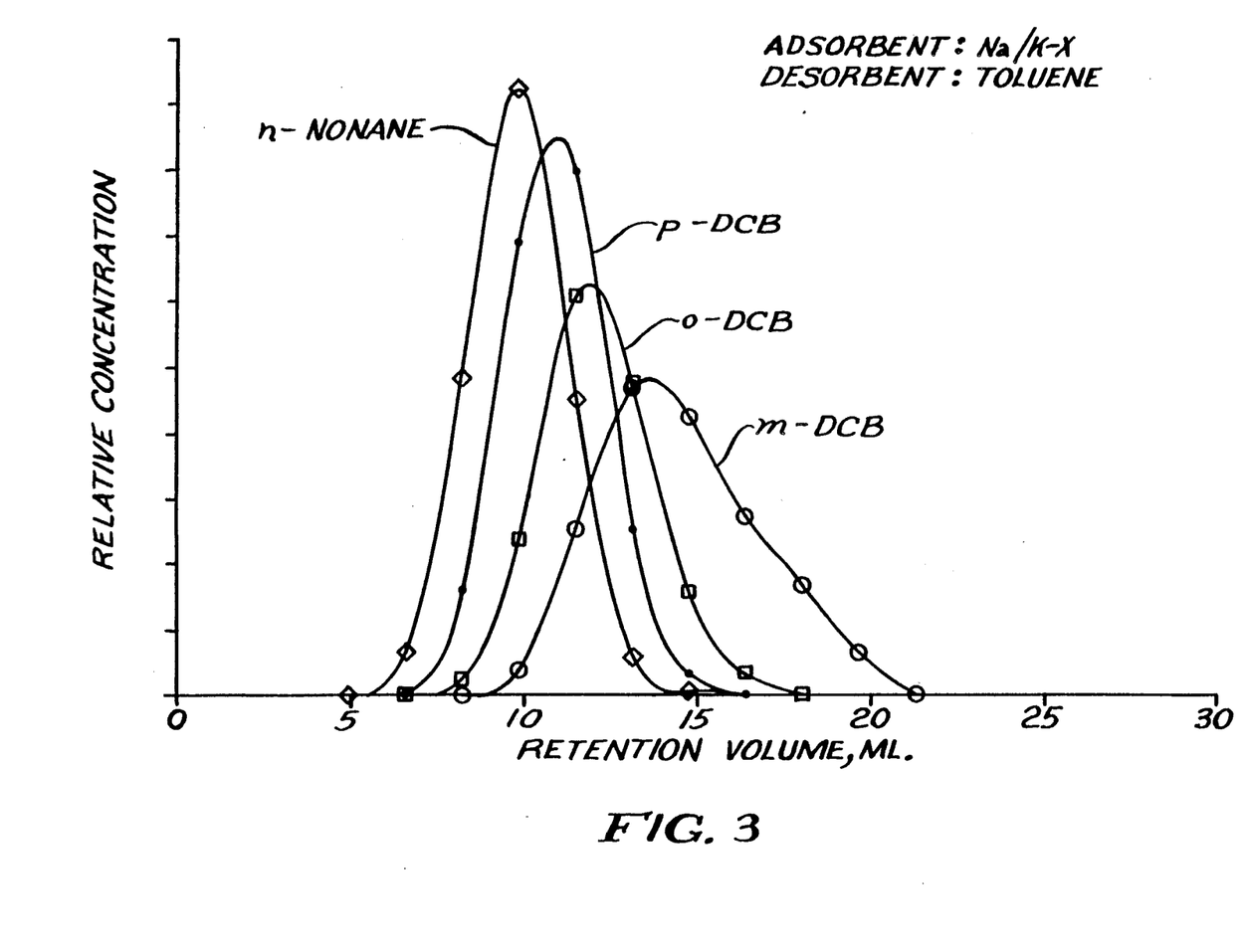

In the first pulse test, the column was filled with 14.5 cc of the type X zeolite mentioned above having potassium cations at cation exchange sites and sodium ions at the remainder of the exchange sites. The adsorbent analyzed 9.75% (wt.) sodium and 5.08% (wt.) potassium, i.e., a weight ratio of 1.9:1. The temperature was maintained at 120° C. and the pressure was sufficient to provide liquid-phase operations. The feed mixture employed for this test contained 2 g of each DCB isomer and 1 g of tracer n-nonane. The desorbent material was toluene. The apparatus conditions and feedstock were the same for the second and third tests with the only differences being in the sodium to potassium weight ratio. In the second test, the adsorbent analyzed 8.77% (wt.) sodium and 7.07% (wt.) potassium. In the third test, the adsorbent analyzed 5.99% (wt.) sodium and 9.14% (wt.) potassium. The sodium to potassium weight ratios in the second and third tests were 1.24 and 0.65, respectively. The operations taking place for each test were as follows. The desorbent material was run continuously at a nominal liquid hourly space velocity (LHSV) of 3.4 which amounted to a flow rate of about 0.81 cc flow rate of desorbent per minute. At some convenient time interval, the desorbent was stopped and 1.0 cc of the feed mixture was run for a 1.23 minute interval at a rate of 0.81 cc per minute. The desorbent stream was then resumed at 3.4 LHSV and continued to pass into the adsorbent column until all of the feed components had been eluted from the column as determined by observing the chromatograph generated by the effluent material leaving the adsorption column. The sequence of operations usually takes about an hour. The pulse of feed and subsequent desorption may be repeated in sequence as often as is desired. The chromatograph tracings obtained from Pulse Tests 1,2 and 3 are shown in the attached FIGS. 1, 2 and 3, respectively. The tracings of FIGS. 1-3 show the separation of m-DCBs, the selectively adsorbed component, from the remaining isomers and dichlorotoluene. The results are also set forth in Table 2.

EXAMPLE II

Figure 4:
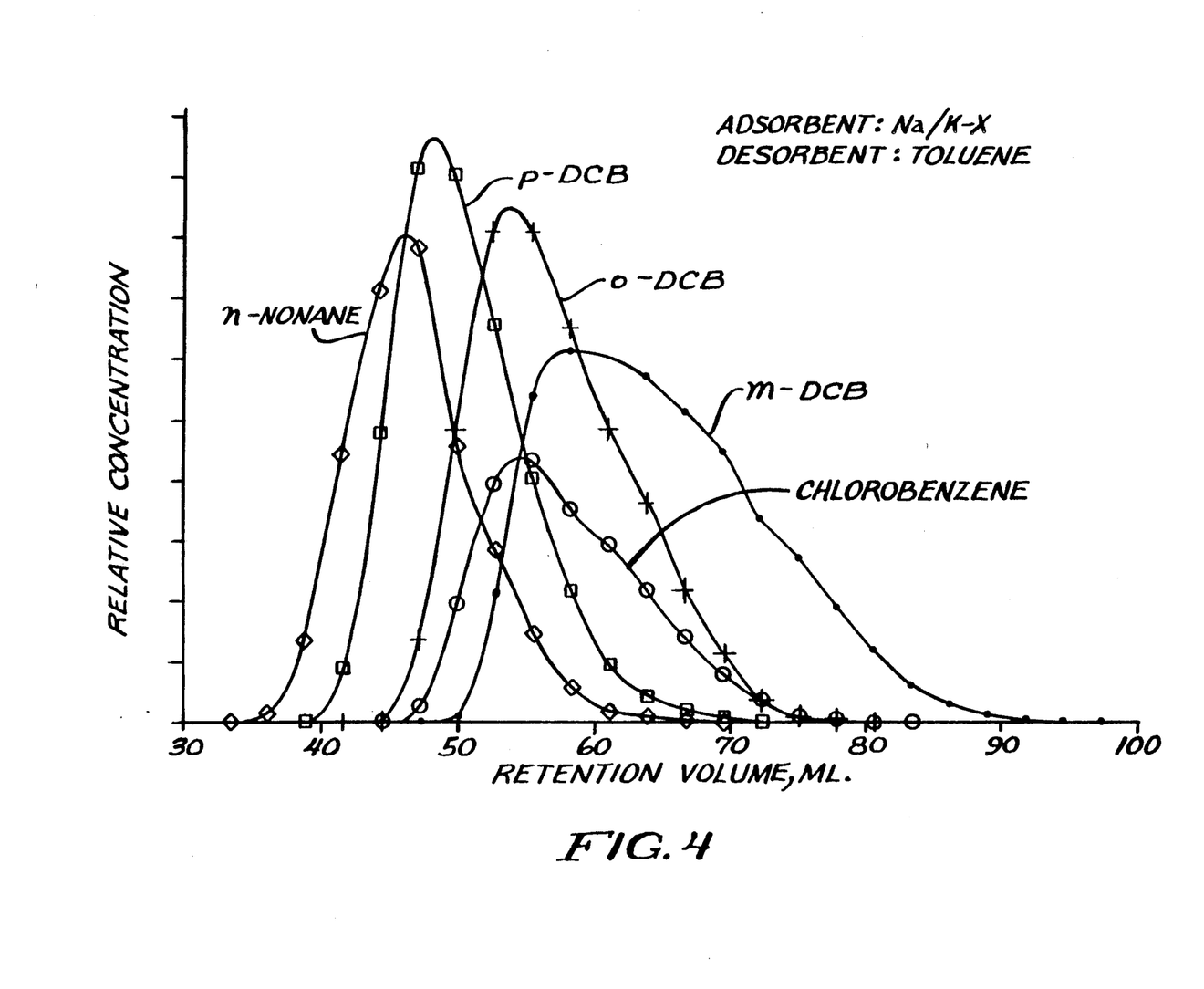
FIG. 4 is similar to FIGS. 1-3 except that the molar ratio of silica to alumina is 2:0 and weight ratio of sodium to potassium is 2.68:1.

To demonstrate the effect of the silica/alumina molar ratio on the adsorptive separation process, an additional pulse test was performed with an X zeolite exchanged with a mixture of sodium and potassium ions under the same conditions of Example I, except that 69.5 cc adsorbent was used in a larger column, the desorbent flow rate was 1.39 cc/min and the temperature was 150° C. The molar ratio of silica to alumina was 2.0. The feed pulse was 5 cc of a mixture of 2 g of each DCB isomer, 2 g chlorobenzene, 1 g nonane and 13 g toluene. The adsorbent analysed 10.8% (wt.) sodium and 7.4% (wt.) potassium, in a Na:K weight ratio of 1.46. The results of the pulse test are shown in FIG. 4 and Table 2.

EXAMPLE III (Comparative)

In order to compare the selective adsorption of DCB isomers with the invention as illustrated in Examples I and II with an X zeolite adsorbent containing only potassium at the exchangeable sites, additional pulse tests were performed with the feed mixtures noted below.

Figure 5:
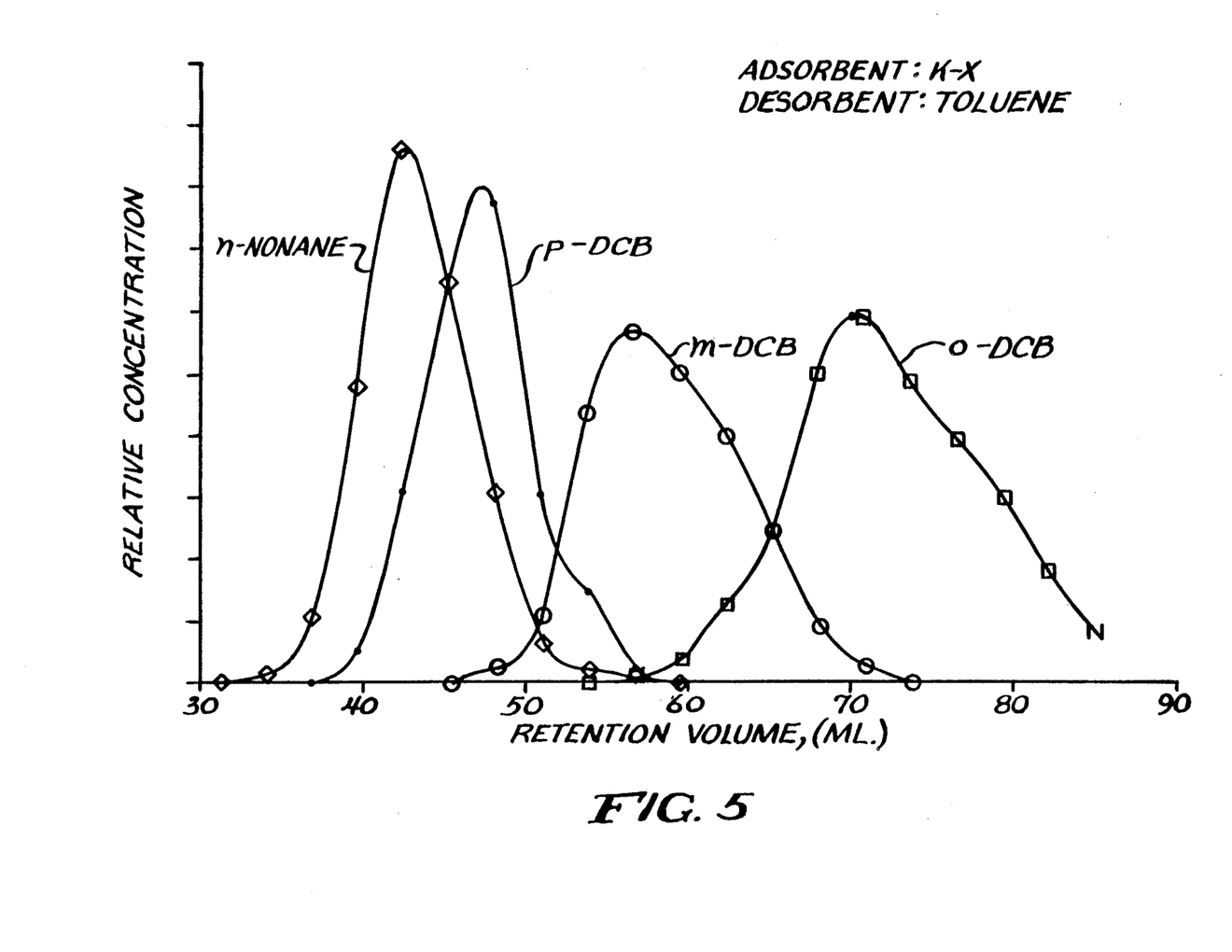
FIGS. 5 and 6 are chromatographic traces representing the comparative separations of Example III with K-exchanged X zeolites at $SiO_2/Al_2O_3$ ratios of 2.5 and 2.0, respectively.

For the first pulse test the column was filled with 69.5 cc of the same adsorbent as Example I having a silica:alumina ratio of 2.5 except that the ion exchange sites were all filled with potassium and analyzed 0% sodium. The column was maintained at a temperature of 150° C. and a pressure sufficient to maintain liquid-phase operations. The feed mixture employed for the test contained 4% (vol) each of m-DCB, o-DCB and p-DCB, 2% (vol.) n-nonane (tracer) and the remainder was desorbent, toluene. Feed pulse and column flow rate was the same as Example II. The desorbent material was toluene. The chromatographic trace obtained is shown in FIG. 5.

Figure 6:
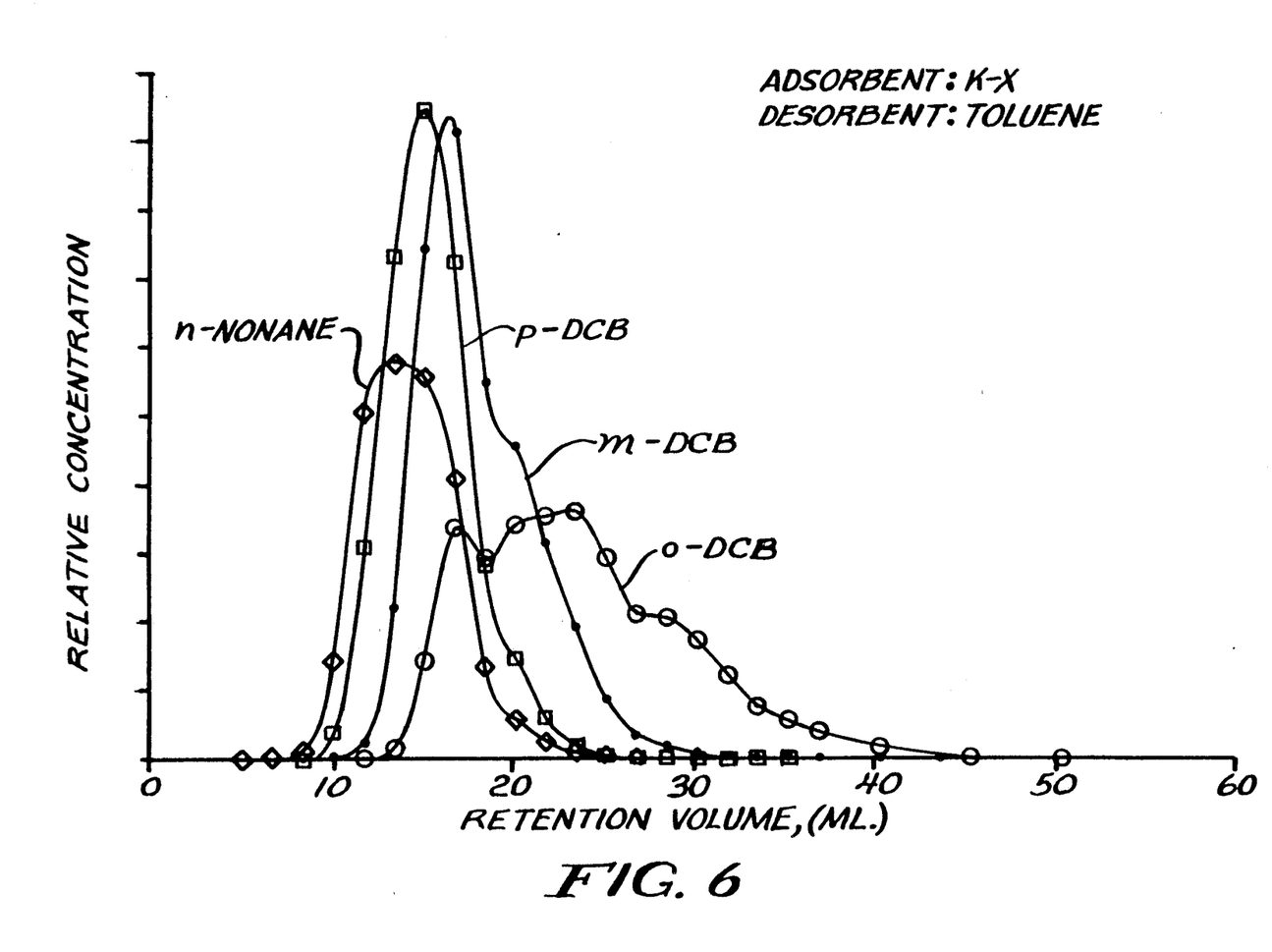

For the second pulse test, the column was filled with 14.5 cc of the same adsorbent as Example II ($SiO_2/Al_2O_3$ molar ratio of 2.0) except that the ion exchanged sites were all filled with potassium and analyzed 0% sodium. The column was maintained at a temperature of 120° C. and a pressure sufficient to maintain liquid phase. A 1 cc pulse of the same feed mixtures as in Example I was used and column flow rate and desorbent were the same as Example I. The chromatographic trace obtained is shown in FIG. 6. The results of both pulse tests are also presented in Table 2 below.

In each of the separations of this example, o-DCB is the preferentially adsorbed isomer, whereas with applicants' mixed ion adsorbents of Examples I and II, m-DCB is preferentially adsorbed.

TABLE 2

| FIG. No. | Ex No. | Sieve | $SiO_2$ $Al_2O_3$ (molar) | % Na | % K | Na/K | NRV (ml) | | | Beta m/o | Beta m/p |
|---|---|---|---|---|---|---|---|---|---|---|---|
| | | | | | | | o-DCB | m-DCB | p-DCB | | |
| 1 | I | NaKX | 2.5 | 9.74 | 5.08 | 1.9 | 3.0 | 5.3 | 1.4 | 1.8 | 3.8 |
| 2 | I | NaKX | 2.5 | 8.77 | 7.07 | 1.24 | 3.3 | 6.2 | 1.5 | 1.9 | 4.1 |
| 3 | I | NaKX | 2.5 | 5.99 | 9.14 | 0.65 | 2.3 | 4.4 | 1.0 | 1.9 | 4.4 |
| 4 | II | NaKX | 2.0 | 10.8 | 7.4 | 1.46 | 10.0 | 17.4 | 3.5 | 1.7 | 5.0 |
| 5 | III | KX | 2.5 | 0 | 17.6 | — | 29.4 | 15.3 | 3.6 | 0.5 | 4.3 |
| 6 | III | KX | 2.0 | 0 | 19.7 | — | 8.5 | 3.0 | 0.9 | 0.4 | 3.3 |

We claim as our invention:

1. A process for separating m-dichlorobenzene from feed mixtures of m-dichlorobenzene and at least one other isomer of dichlorobenzene which process comprises contacting said feed mixture at adsorption conditions, including a temperature of from about 20° C. to about 250° C. and a pressure sufficient to maintain liquid phase with an adsorbent comprising an X-type zeolite exchanged with a mixture of sodium and potassium ions at the cation exchange sites at a weight ratio of sodium to potassium in the range from 0.65:1 to 2:1, selectively adsorbing said m-dichlorobenzene more strongly than said other isomers, removing the relatively non-adsorbed portion of the feed mixture from contact with the adsorbent, and thereafter recovering m-dichlorobenzene from the adsorbent by contacting said adsorbent, at desorption conditions, including a temperature of from about 20° C. to about 250° C. and a pressure sufficient to maintain liquid phase, with an alkylbenzene desorbent.

2. The process of claim 1 wherein one of said other isomers of dichlorobenzene is ortho-dichlorobenzene.

3. The process of claim 1 wherein said desorbent is toluene.

4. The process of claim 1 wherein said separation is effected by means of a simulated moving bed system.

5. The process of claim 1 wherein the simulated moving bed uses a countercurrent system.

6. The process of claim 1 wherein the simulated moving bed uses a cocurrent system.

* * * * *